United States Patent [19]

Davis et al.

[11] 4,376,059
[45] Mar. 8, 1983

[54] PROCESS FOR PREPARING ARTIFICIAL RED CELLS

[75] Inventors: Thomas A. Davis, Scotch Plains; William J. Asher, Fanwood, both of N.J.

[73] Assignee: Exxon Research and Engineering Co., Florham Park, N.J.

[21] Appl. No.: 139,454

[22] Filed: Apr. 11, 1980

[51] Int. Cl.$^3$ .................. B01J 13/02; A01N 25/28; A61K 9/50; A61K 9/64
[52] U.S. Cl. .................................... 252/316; 424/36; 424/177
[58] Field of Search .................. 252/316; 424/36, 177

[56] References Cited

U.S. PATENT DOCUMENTS 3,879,510 4/1975 Kitajima et al. .................. 424/11 X
4,061,736 12/1977 Morris et al. ............ 260/112.5 R X
4,133,874 1/1979 Miller et al. .................... 424/365 X

FOREIGN PATENT DOCUMENTS 873815 6/1971 Canada ................................ 252/316
1540461 2/1979 United Kingdom ................ 252/316

OTHER PUBLICATIONS

Chang: "Artificial Cells", Chemtech, Feb. 1975, pp. 80–85.
Chang et al.: "Semipermeable Aqueous Microcapsules", Canadian Journal of Physiology and Pharmacology, vol. 44 (1966), pp. 115–128.

Primary Examiner—Richard D. Lovering
Attorney, Agent, or Firm—Edward M. Corcoran

[57] ABSTRACT

A process for preparing artificial red cells comprising microdroplets of aqueous, stroma-free hemoglobin solution encapsulated in membranes of polymerized hemoglobin, said process comprising forming microdroplets of hemoglobin solution in a continuous oil phase, cross-linking the hemoglobin at the surface of the microdroplets with a suitable cross-linking agent to form the artificial red cells and recovering the cells. In one embodiment, a liquid membrane encapsulation technique employing a water-soluble cross-linking agent is used to form the cells. In another embodiment an oil-soluble cross-linking agent is present in the oil phase containing the hemoglobin microdroplets.

9 Claims, No Drawings

PROCESS FOR PREPARING ARTIFICIAL RED CELLS

FIELD OF THE INVENTION

This invention relates to a process for preparing artificial red cells. More particularly, this invention relates to process for preparing artificial red cells of aqueous hemoglobin solution encapsulated in membranes of polymerized hemoglobin. Still more particularly, this invention relates to preparing artificial red cells comprising microdroplets of aqueous hemoglobin solution encapsulated in membranes of polymerized, cross-linked hemoglobin by forming microdroplets of hemoglobin solution in oil and cross-linking the hemoglobin at the surface of the microdroplets with a suitable cross-linking agent.

BACKGROUND OF THE INVENTION

The search for blood substitutes has been prompted by many serious drawbacks to the use of donor blood. One of the most serious problems relates to the fact that an adequate supply of compatible donor blood may not be available at the time and place where it is needed. This would be a particularly serious problem during periods of disaster or war when blood is most needed. The incompatibility of different blood types and the relatively short storage life of whole blood limits the practicability of collecting and storing large amounts of whole blood. According to some estimates, as much as 30% of human blood collected is not reinfused into human patients. Although red blood cells have a relatively short storage life which contributes to a large amount of wasted blood, the hemoglobin contained in the red cells appears to be unaffected if stored under the proper conditions. However, the red cell membranes tend to degrade in storage. Further, the transmission of disease, especially hepatitis, is a problem that makes physicians hesitant to transfuse whole blood or plasma into patients under conditions that are not life-threatening to the patient. Thus, there is a definite need for effective blood substitutes.

The primary function of a plasma expander or blood substitute is to maintain an adequate circulation volume of a solution that is nontoxic to the human body and which will transport oxygen throughout the body to sustain life until the body can remanufacture a supply of natural blood. Artificial blood substitutes have received considerable attention during the last decade. The development of fluorochemical emulsions that transport oxygen and carbon dioxide in the blood stream offered hope of a viable blood substitute. Unfortunately, however, a number of problems have limited the use of fluorochemical emulsions in human patients.

Aqueous hemoglobin solution is the main constituent of red blood cells and is the blood's oxygen carrier. It has also been demonstrated to be safe when used in human patients. However, its intravascular persistance and oxygen-release characteristics have proven to be inadequate. Free hemoglobin completely disappears from the blood stream in less than about eight hours and its affinity for oxygen is much greater than that of an equivalent amount of hemoglobin encapsulated within the natural red-blood-cell membrane. This greater affinity makes liberation of oxygen to the tissues much more difficult. It is the red-blood-cell membrane that contains the antigenic material which causes problems when mismatching of donor and recipient occurs. Problems of intravascular coagulation and renal damage have been demonstrated to be caused by the stroma present in such membranes and not the hemoglobin molecule itself. Thus, the use of stroma-free hemoglobin solution (SFHS) as a blood substitute offers many potential advantages regarding immunology, storage and bio-compatibility. Also, since free hemoglobin is not toxic to the kidney, SFHS seems an ideal starting material for a blood substitute.

A number of attempts have been made using standard encapsulated techniques employing various polymeric materials such as celluloses, polystyrenes and polyamides to create artificial red cells by encapsulating hemoglobin therein. However, these standard encapsulation techniques have produced red cells non-biodegradable by ordinary metabolism. Alternatively, U.S. Pat. Nos. 4,001,401; 4,053,590; and 4,061,736 disclose blood substitutes and plasma expanders comprising polymerized, cross-linked, stroma-free hemoglobin in either the oxyhemoglobin or deoxyhemoglobin form, said polymers having a molecular weight ranging from about 64,000 to 1,000,000. These blood substitutes are prepared by cross-linking stroma-free hemoglobin in bulk solution with a suitable cross-linking agent that is at least bifunctional in nature. However, the hemoglobin polymers are not artificial red cells, because they are merely polymeric molecules as such and do not consist of a membrane encapsulating a fluid phase which can reversibly combine with oxygen. In another attempt at creating artificial red cells, Miller et al in U.S. Pat. No. 4,133,874 disclose forming artificial red cells by encapsulating hemoglobin in liquid lipid materials comprising phospholipids, and optionally cholesterol, to form cells typically ranging from 0.1 to 10 microns in their greatest dimension. The lipid material is said to form a continuous membrane around the hemoglobin solution. However, phospholipids have a tendency to release their contents into other cells in the body. Kitajima et al in U.S. Pat. No. 3,879,510 show reinforcing the naturally-occurring membrane around red blood cells by reacting the membrane with an isocyanate such as toluene diisocyanate. In reinforcing the naturally occurring membrane, red blood cells are dispersed in a suitable isotonic or hypertonic saline solution to which is added an oil-in-water emulsion of liquid polyisocyanate which reacts with the membranes, thereby reinforcing same. However, it is the red blood cell membranes which contain materials that cause short storage life, and incompatibility problems between different blood types.

Thus, there is a need for artificial red cells comprising an encapsulated, stroma-free hemoglobin solution of a suitable size, strength and flexibility to permit same to be used effectively as blood substitutes.

SUMMARY OF THE INVENTION

The present invention relates to a process for preparing artificial red cells comprising microdroplets of stroma-free, aqueous hemoglobin solution encapsulated in membranes of cross-linked, polymerized hemoglobin, said process comprising forming microdroplets of hemoglobin solution in a continuous oil phase, cross-linking hemoglobins at the surface of the microdroplets with a suitable cross-linking agent to form the artificial red cells and recovering the cells. In one embodiment of the process of this invention a liquid membrane technique employing a water-soluble cross-linking agent is used to form the cells. In this process, a stroma-free, aqueous hemoglobin is emulsified in oil, the emulsion is suspended in an aqueous suspending phase containing the cross-linking agent to form the red cells and the red cells are recovered. In another embodiment of the process of this invention, microdroplets of the hemoglobin solution are formed in an oil phase and an oil-soluble cross-linking is added to the oil phase either before or after contacting the oil phase with the hemoglobin solution and forming the dispersion of microdroplets of hemoglobin solution in the oil phase.

It should be understood that the process of this invention extends to encapsulating any cross-linkable proteinaceous material, in which case the cell size may broadly range from about 0.1 to 100 microns.

As a further embodiment of this invention, the artificial red cells or encapsulated proteinaceous material made flexible and readily deformable in nature by contacting them with an aqueous solution with respect to which the encapsulated material is hypotonic.

DETAILED DESCRIPTION OF THE INVENTION

One process for preparing the artificial red cells of this invention is by the use of a liquid membrane encapsulation technique. In this method, the stroma-free hemoglobin is emulsified in a surfactant-containing oil to form discrete, red-cell-size microdroplets of hemoglobin in a continuous oil phase. In general, this process comprises the steps of:

(a) emulsifying a stroma-free, aqueous hemoglobin solution in a surfactant-containing oil to form an emulsion comprising discrete microdroplets of said hemoglobin solution in a continuous phase of said oil;

(b) forming, in an aqueous suspending phase, liquid membrane capsules comprising globules of said emulsion formed in (a), said globules comprising an aqueous interior phase of discrete microdroplets of hemoglobin solution and an exterior oil phase immiscible with both said aqueous interior phase and said suspending phase and wherein said suspending phase contains a water soluble cross-linking agent capable of polymerizing hemoglobin;

(c) forming artificial red cells suspended in said globules of oil phase by maintaining said capsules in said aqueous suspending phase for a time sufficient for said cross-linking agent to polymerize hemoglobin at the surface of said hemoglobin solution microdroplets present in said capsule to form an artificial membrane around each of said microdroplets of hemoglobin solution;

(d) separating said suspending phase from said oil phase containing the artificial red cells; and (e) recovering the artificial red cells from the oil phase.

However, it should be noted that if the oil used to form the emulsion is a lipid, such as a phospholipid, it may not be necessary to use a surfactant in the oil. As a further note, if the hemoglobin is emulsified in a phospholipid instead of in an oil/surfactant combination, the liquid membrane capsules formed in step (b) could be regarded as being similar in structure to certain types of liposomes.

The cross-linking agent may be in the suspending phase when the liquid membrane capsules are formed or it may be added to same after said capsules are formed. The amount of cross-linking agent added to the suspending phase may be just enough to form an artificial membrane of polymerized hemoglobin around each microdroplet of hemoglobin emulsified in the oil globule or it may be present in amounts substantially in excess of that required to form the artificial membranes. In the latter event the reaction will be stopped or quenched after a suitable predetermined period by separating the aqueous suspending phase from the oil phase containing the artificial red cells, by diluting the aqueous suspending phase, by adding a material which reacts with the remaining cross-linking agent, or by a combination of these methods. It is believed that the cross-linking agent dissolved in the oil diffuses to the interface between the oil and the microdroplets of hemoglobin solution. As has hereinbefore been stated, the cross-linking agent or agents must have at least two functional groups capable of reacting with the amine groups of lysine residues which are located at numerous sites of the hemoglobin molecule. The cross-linking agent must form intermolecular cross-links, although some intramolecular cross-links can be tolerated. The cross-linking of the hemoglobin at the surface of each microdroplet forms a film or membrane of polymerized hemoglobin that effectively encapsulates the stroma-free hemoglobin solution, thereby forming artificial red cells.

Important to the process of this invention is separating the artificial red cells from the oil phase in which they were formed. This may be done by separating the suspension of artificial red cells in the oil phase from the aqueous suspending phase and washing the suspension several times with an appropriate solution such as isotonic saline solution to remove any unreacted cross-linking agent. The washed suspension is then contacted with a second aqueous phase in the presence of a second surfactant under conditions of agitation to form, suspend and break globules of the artificial red cell-containing oil phase in said second suspending phase. Alternatively, the second surfactant can be added directly to the artificial red cell-containing oil phase prior to its contact with the suspending phase. However, better results appear to be obtained if the second surfactant is added to the second aqueous suspending phase. In practice it has been found that a saline solution is an effective second aqueous suspending phase and that when the breaking emulsion is agitated with a large quantity of the saline solution to which the second surfactant has been added, the artificial red cells become suspended in the saline suspending phase. At this point, the artificial red cells may also require treatment with one or more reagents to deactivate unreacted functional groups of the cross-linking agent or to modify the surface characteristics of the membranes. The artificial red cells may be recovered from the suspending solution by centrifugation, filtration, decanting or any suitable separation technique and may then be either freeze-dried or resuspended in a suitable solution.

Optionally, if the first suspending phase contained only enough cross-linking agent to form the artificial red cells, it is not required that a second suspending phase be employed to free the cells. In this case, the second surfactant may be added to the first suspending phase to free the red cells.

It is extremely important in the process of recovering the artificial red cells from the oil that the surfactant employed with the second suspending phase (or added to the first suspending phase if only enough cross-linking agent was present therein to form the artificial red cells) have an HLB at least 9, preferably at least 11 and more preferably at least 13. That is, the surfactant added to the aqueous suspending phase which breaks up the oil phase and frees the artificial red cells must be preferentially soluble in the aqueous phase and not the oil. As is known in the art, this preferential water solubility can readily be defined in terms of HLB. It is believed that the second surfactant having an HLB of at least 9 destabilizes the suspension of artificial red cells in the oil thereby releasing the red cells and forming a three-phase system comprising an aqueous, surfactant-containing suspending phase, an oil phase and the artificial red cells.

Yet another process for making the artificial red cells of this invention comprises emulsifying a stroma-free aqueous hemoglobin solution in a surfactant-containing oil to form an emulsion comprising microdroplets of hemoglobin solution dispersed in a continuous phase of said oil wherein said oil phase contains a cross-linking agent which polymerizes the hemoglobin at the surface of said microdroplets to form artificial red cells dispersed in said oil phase. In this process, the cross-linking agent can either be initially present in the oil or can be added to the oil after the hemoglobin microdroplets have been formed therein. In this process, it is quite naturally necessary for the cross-linking agent to be oil soluble. As was the case for the liquid membrane encapsulation technique described above, just enough cross-linking agent can be added to the oil to effectively cross-link the hemoglobin at the surface of the emulsified microdroplets, or the cross-linking agent or agents can be present in sufficient excess such that the reaction has to be quenced by diluting the oil, by quickly separating the so-formed artificial red cells from the oil, by adding to the oil a material which reacts with the remaining cross-linking agent, by contacting the emulsion with an aqueous suspension phase containing the second surfactant under conditions of agitation to break the emulsion, or a combination of these methods.

The artificial red cells of this invention may also be formed by starting with liposomes containing hemoglobin solution suspended in a suitable suspending phase. In this case, the liposomes are contacted with a suitable cross-linking agent to form artificial red cells therein using the same procedure as with the liquid membrane encapsulating technique, except that one would start with step (c) of said procedure after adding the cross-linking agent to the suspending phase. The so-formed suspension of artificial red cells in lipid may then be broken and the artificial cells freed by contacting the suspension with an aqueous solution in the presence of a surfactant having an HLB of at least 9 as hereinbefore set forth.

The artificial red cells of stroma-free, aqueous hemoglobin solution encapsulated in membranes of cross-linked, polymerized, stroma-free hemoglobin produced by the process of this invention are permeable to oxygen and impermeable to hemoglobin. These artificial red cells can be prepared having diameters of less than 8 microns in their greatest dimension, preferably less than 4 microns and are able to maintain their individual integrity under conditions of flow with shear rates of up to about $2 \times 10^5$ sec$^{-1}$. If desired, they may consist essentially of a stroma-free, aqueous hemoglobin solution encapsulated in cross-linked hemoglobin, thus consisting essentially of stroma-free hemoglobin and minute amounts of cross-linking agent. Alternatively, other ingredients such as drugs, nutrients, hormones, enzymes and antibodies may be incorporated into the hemoglobin solution prior to the encapsulation thereof. These artificial red cells may be prepared by emulsifying stroma-free hemoglobin solution, as microdroplets, in an oil phase, reacting a suitable cross-linking agent with the hemoglobin at the surface of the microdroplets of emulsified hemoglobin solutions thereby forming a suspension of artificial red cells in the oil and then recovering the artificial red cells. It should be understood however, that the scope of this invention also extends to encapsulating any cross-linkable proteinaceous material, in which case the cell size may broadly range from about 0.1 to 100 microns. Further, the artificial red cells or microdroplets of encapsulated proteinaceous material of this invention may be made flexible and easily deformable in nature simply by contacting them with an aqueous solution to which the encapsulated hemoglobin solution or solution of proteinaceous material is hypotonic. Thus, contacting same with an aqueous solution with respect to which the hemoglobin or proteinaceous material solution is hypotonic causes some of the water in the encapsulated solution to osmotically diffuse through the membrane into the aqueous solution which depletes the interior of the artificial red cell or microdroplet of encapsulated proteinaceous material of a portion of its contents, thus rendering the cell flexible and readily deformed.

Hemoglobin solution useful for the artificial red cells of this invention is prepared by starting with red blood cells separated from freshly drawn human blood, from outdated whole blood, packed red cells obtained from human donor centers or from red blood cells obtained from animal blood such as bovine blood. There are many known ways to prepare stroma-free hemoglobin. In one particular method, whole blood is drawn into bottles containing an anticoagulant, centrifuged and the supernatent plasma withdrawn. Next, the resultant red cells are washed in about 1 to 4 volumes of cold, isotonic or hypertonic sodium chloride solution to form a suspension of red cells which is then centrifuged and the supernatant removed and discarded. The red cells are generally washed an additional two to three times with the wash being discarded after each centrifugation. Procedures for preparing stroma-free hemoglobin solution (SFHS) involve hemolysis, centrifugation, filtration and, optionally, dialysis. To obtain stroma-free hemoglobin, the red blood cells are first lysed in about one to four volumes of cold water or other lysing solutions such as hypotonic phosphate buffers or hypotonic saline. After lysing, the red cell suspension is shaken and cold toluene is added at about 10–200 volume percent of the red cells, usually about 10–30 volume percent. This mixture is then shaken for four to ten minutes and left standing at from 4° C. to 6° C. for 24 to 72 hours to produce a triphasic mixture. A lower, clearer, red layer is isolated and centrifuged at about 40,000 to 50,000 g for at least 60 minutes at about 4° C. to 6° C. Then, the upper supernatant is separated and filtered through a suitable filter such as a diatomaceous earth filter. If desired, residual low molecular weight salts and metabolites may be removed from the stroma-free hemoglobin by dialysis against standard or medically acceptable buffers which are well known to those in the art. The method used to prepare SFHS to demonstrate the instant invention is set forth in Example 6 supra.

Suitable cross-linking agents include those which are at least bifunctional and, for the case where one desires to form artificial red cells, those which result in a cross-linked hemoglobin membrane which is biodegradale in a mammalian body so that the cells can be eliminated from the body after their function has been performed. The bi or poly-functional cross-linking agents must have at least two functional groups which can be the same or different. These groups must be capable of reacting with and cross-linking the functional groups of the proteinaceous material which, in the case of hemoglobin, are primarily amino groups. By amino groups is meant the N-terminal alpha amino group of the hemoglobin chains and those of the basic amino acid residues such as lysine and arginine. The following are intended to be illustrative, but non-limiting examples of various categories of suitable cross-linking agents.

The functional groups of the cross-linking agent can be covalently bonded to each other or they can be separated by an aliphatic or by an aromatic ring. Exemplary aromatic stabilized functional groups are azo and halo activated with a nitro group. These include compounds having a heterocyclic ring with reactive groups bonded to the ring. For example, triazines of the formula:

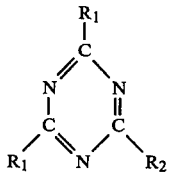

wherein $R_1$ is halogen including fluoro, chloro and bromo, and $R_2$ is a nucleophilic substitute such as an aliphatic or aromatic group, a halogen, a lower alkyl of 1 to 8 carbons, and amino. Cross-linking agents embraced by this formula are 2-amino-4-,6-dichloro-s-triazine and chloro-s-triazine. The cross-linking agents include aromatic stabilized agents prepared by the diazotation of an aromatic diamine, for example, benzidine and its derivatives with nitrous acid to yield bis-diazobenzidines of the formula:

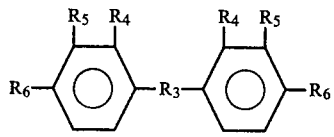

wherein $R_3$ is a member selected from the group consisting of a covalent bond, alkylene of 1 to 5 carbons, phenylene, ether, sulfone and secamine, $R_4$ is halogen or nitro. $R_5$ is hydrogen, nitro, lower alkyl of 1 to 8 carbons, sulfonate ($SO_3H$) and carboxylate, and $R_6$ is halogen, diazo (—N:N—), isocyanate (NCO), and isothiocyanate (NCS). Representative agents embraced by the formula include bisdiazobenzidine 2,2'-sulfonic acid, 4,4'-difluoro-3,3'-dinitrophenylsulfone and diphenyl-4,4'-diisothiocyanate.

Cross-linking agents suitable for the invention include compounds of the formula:

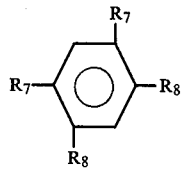

wherein $R_7$ is halogen and $R_8$ is nitro, or hydrogen with at least one $R_8$ a nitro, as represented by the commercially available activated halogenated reagent 1,5-difluoro-2,4-dinitrobenzene.

Cross-linking agents suitable for the purpose of the invention also include compounds of the formula $(R_9)_2C=O$ wherein $R_9$ is hydrogen or halogen, and compounds of the formula $R_{10}-(CH_2)_n-R_{10}$ wherein $R_{10}$ is the same or different and n is 1 to 8. The agents also include compounds having a functional group bound to an aromatic moiety either directly or through an alkylene bridge of the formula $R_{10}-(CH_2)_m-C_6H_4-(CH_2)_m-R_{10}$ wherein $R_{10}$ is the same or different and m is 0 to 3. Cross-linking agents include the compounds having the functional groups bonded to a cycloalkyl as represented by the formula:

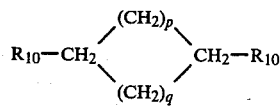

wherein $R_{10}$ is the same or different, p is 0 to 4, and q is 1 to 4. The cross-linking agents include compounds having functional groups bonded to an aliphatic chain interrupted with a nonfunctional group or having nonfunctional groups bonded to the chain as represented by compounds of the formula $R_{10}-(CH_2)_x-R_{11}-(CH_2)_x-R_{10}$ wherein $R_{10}$ is the same or different, $R_{11}$ is selected from the group consisting of an ether bridge, an divalent amine and a sulfone, and x is an alkylene of 1 to 5 carbon atoms, which each x the same or different. Representative of the functional group embraced by $R_{10}$ include isocyanate, vinyl, imine, isothiocyanate, isocyanide, aldehyde, epoxide, chloroformate, thiochloroformate, and imido lower alkyl ester, and thiolactones of the formula:

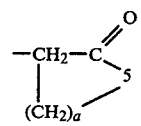

wherein a is 1 to 3. Also, $R_{10}$ can be an activated group formed by reacting the carboxylic acid with a thionyl halide or phosphorus halide, or an activated group formed by reacting an amide or an alkyl ester of the carboxylic acid with hydrazine and then with nitrous acid to yield the corresponding activated group $COR_{12}$ wherein $R_{12}$ is halogen or azide. The activated group can also be formed by reacting the carboxylic acid with N,N'-carbonyl diimidazole or a carbodiimide of the formula $R_{13}-N=C=N-R_{13}$ wherein $R_{13}$ is the same or different and are a lower alkyl, a lower cycloalkyl, di(lower)alkyl amino lower alkylene, and heterocyclic lower alkyl including morpholino ethyl. $R_{12}$ can also be a

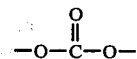

lower alkyl, and a

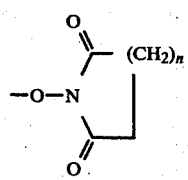

wherein n is 1 or 2.

Exemplary commercially available cross-linking reagents embraced by the above formula include divinyl sulfone, epichlorohydrin, butadiene diepoxide, ethylene glycol diglycidyl ether, glycerol diglycidyl ether, dimethyl suberimidate dihydrochloride, dimethyl malonimidate dihydrochloride, and dimethyl adipimidate dihydrochloride.

Representative of compounds bearing a functional isocyanate or isothiocyanate group are the compounds listed below. Additionally, the isocyanates or isothiocyanates can be synthesized by reacting an alkyl or aryl amine with phosgene or thiophosgene. The isocyanates used for cross-linking are diisocyanates and they react with the free amino groups of hemoglobin producing urea or thiourea cross-linked sites. Typical compounds include diphenyl-4,4'-diisothiocyanate-2,2'-disulfonic acid, toluene diisocyanate, toluene-2-isocyanate-4-isothiocyanate, 3-methoxydiphenylmethane-4-4'-diisocyanate, propylene diisocyanate, butylene diisocyanate, and hexamethylene diisocyanate.

Exemplary of cross-linking agents having an aldehyde or dialdehyde functionality include formaldehyde, paraformaldehyde, formaldehyde activated ureas such as 1,3-bis(hydroxymethyl) urea, N,N'-di(hydroxymethyl) imidazolidinone prepared from formaldehyde condensation with a urea according to the formula $CH_2O + R_{16}HN—NHR_{16} \rightarrow HOCH_2NR_{16}—CO—NR_{16}—CH_2OH$ wherein $R_{16}$ is hydrogen, alkyl, aryl or heterocyclic ring. Other dialdehyde cross-linking agents include dialdehydes of the formula $OCH—R_{17}—HCO$ wherein $R_{17}$ is member selected from the group consisting of a covalent bond and a straight or branched chain alkylene of 1 to 8 carbons. Dialdehydes embraced by the formula include glyoxal, malonic dialdehyde, succinic dialdehyde, glutaraldehyde, adipaldehyde, 3-methyl glutaraldehyde, propyladipaldehyde, phthalic dialdehyde, terephthaldehyde and malonic dialdehyde.

Other cross-linking agents include derivatives of carboxylic acids and carboxylic acid residues of hemoglobin activated in situ to give a reactive derivative of hemoglobin that will cross-link with the amines of another hemoglobin. Typical carboxylic acids useful for this purpose have the formula $CO_2H(CH_2)_nCO_2H$, and $\{(CH_2)_nCOOH\}_3CH$ wherein n is 1 to 8. The carboxylic acids include citric, malonic, adipic and succinic. Carboxylic acid activators include thionyl chloride, carbodiimides, N-ethyl-5-phenyl-isoxazolium-3'-sulphonate (Woodward's reagent K), N,N'-carbonyldiimidazole, N-t-butyl-5-methylisoxazolium perchlorate (Woodward's reagent L), 1-ethyl-3-dimethyl aminopropylcarbodiimide, 1-cyclohexyl-3-(2-morpholinoethyl) carbodiimide, metho-p-toluene sulfonate. The cross-linking reaction using a carboxylic acid can be represented by the equation

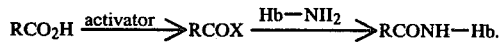

Other cross-linking groups that can be used are prepared from esters and thioesters activated by strained thiolactones, hydroxysuccinimide esters, halogenated carboxylic acid esters and imidates. The above functional reagents or methods for preparing them are reported in Bull. Soc. Chem. Fr., Vol. 12, pages 4615 to 4617, 1971; Biochemical Aspects of Reactions on Solid Supports, by Stark, George R., Chapter 1, published by Academic Press, 1971; Chemtech, pages 47 to 55, 1974; Rev. Pure and Appl. Chem. Vol. 21, pages 83 to 113, 1971; and British Pat. No. 1,252,770.

The oil used in the process of this invention may be any oil such as mineral (preferably paraffinic), refined vegetable refined animal oil, etc. to which the surfactant is added. It is obvious of course that the oil used in preparing the hemoglobin emulsion should be of a type which is inert with respect to the hemoglobin, the surfactant used and the cross-linking agent. It is also obvious that the oil should not contain materials that are toxic to mammalian bodies and which will diffuse into either the hemoglobin solution or into the artificial red cells. Some examples of suitable oils which can be used as a oil for emulsifying the hemoglobin solution include hydrocarbon oils that have been refined to remove toxic ingredients and which have molecular weights up to 1000, such as paraffins, iosparaffins, naphthalenes and non-polynuclear aromatics. Particularly suitable are mineral oils which have been highly refined for use in human ingestion. Additionally, oils or treated oils from animal or vegetable sources may be used provided they meet the criteria set forth above. Silicon fluids can be used. Also, lipids such as phospholipids may be used as the oil. Oils used in the process of forming the artificial red blood cells of this invention may have a viscosity broadly ranging from between about 0.3 to about 1,000 centipoise at normal temperature. A preferred range is from about 1 to 150 and particularly preferred in from about 2 to 20 centipoise.

The oil-soluble surfactant must not dissolve in the hemoglobin or react with the cross-linking agent. This surfactant must be oil-soluble and may be present in the oil from about 0.01 wt. % up to about 50 wt. % and preferably from about 0.5 to 5 wt. % of the oil. A wide variety of surfactants may be used in the oil to emulsify the hemoglobin solution including those described in "Surface Active Agents and Detergents" by Schwartz, Perry and Bush, Inter-sciences Publishers, Inc., New York and in "Surface Chemistry" by Osepow, Reinhold, New York, 1962, Chapter 8. Of course not all the surfactants included in these publications meet the nontoxic and inert or non-transferring criteria set forth above. Surfactants that have been satisfactorily employed to make the artificial red cells of this invention include Santone 10-10-0 which is a decaglycerol decaoleate and is available from the Durkee Industrial Foods Group of SCM Corporation and polyamine derivatives having the general formula:

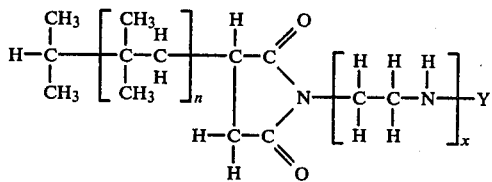

where n varies from 10 to 60, x varies from 3 to 10 and Y is selected from the group consisting of hydrogen and oxygen-containing hydrocarbyl radicals having up to 10 carbons. In particular, higher molecular weight polyamines with the structure of:

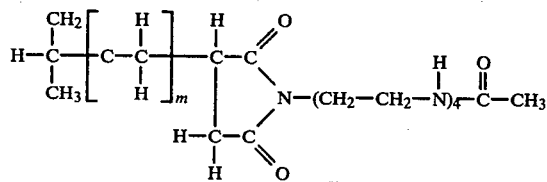

wherein m is an integer of about 40 have been found to be particularly effective. This latter compound was commercially available as ENJ-3029 from Exxon Chemical Company.

The invention will be more readily understood by reference to the examples below.

PREFERRED EMBODIMENT

Example 1

Stroma-free hemoglobin solution (SFHS) was prepared from fresh whole blood from slaughterhouse cattle (bovine blood) which was collected in sterilized 500 ml polypropylene bottles containing 80 ml of an anticoagulant-antibiotic solution comprising 0.73% of citric acid, 2.2% of sodium citrate, 2.45% of glucose, 0.93% of Penicillin "6" USP Potassium (Grant Island Biological Supply Company) and 0.735 g of Streptomycin Sulfate (Grant Island). The blood was immediately refrigerated. Red cells were isolated by centrifuging, washing four times by resuspending them in 1.6% saline solution, centrifuging again, and discarding the supernatant. The packed red cells were then lysed (osmotically ruptured) by the addition of an equal volume of distilled water. Then the stroma (lipids and debris from the red-cell membrane) was removed, from the hemolysate by extracting with cold toluene, centrifugating for 30 min at 4° C., and filtering through membranes of progressively finer porosity down to 0.2 μm to produce the SFHS.

An emulsion of the SFHS in oil was prepared in a mixer comprising a 120 ml glass jar, a shaft-mounted, 3-blade, 3.75-cm-diameter, propeller-type stirrer positioned 0.5 cm from the bottom of the jar, and a 0.32 cm OD dip tube extended through a cap which covered the jar to within 0.5 cm of the bottom of the jar. The distance between the dip tube and the propeller was 0.3 cm. The oil phase was an isoparaffinic mineral oil having a viscosity of about 2 centipoise at 38° C. (Exxon Isopar M) containing 4% of an oil-solube polyamine surfactant (Exxon ENJ 3029). The SFHS was injected through the dip tube over a period of 1 minute into an equal weight of oil contained in the jar while stirred at 4000 rpm. Stirring was continued for 5 minutes to form red-cell-size microdroplets of SFHS in oil.

Liquid membrane capsules were formed in a second stirred-jar device identical to the one used to form the emulsion. The suspending phase was 75 ml of an aqueous solution containing 0.4% of glutaraldehyde in phosphate buffered saline (1% of sodium chloride and 0.74% of sodium biphosphate). A 25-ml batch of the SFHS-in-oil emulsion was injected through the dip tube into the suspending phase which was being stirred at 1,000 rpm. After 5 min the stirrer was stopped, the phases were allowed to separate, and the suspending phase was removed through the dip tube. The artificial red cells remained in the oil phase. To remove unreacted glutaraldehyde, the oil phase was washed three times by the addition of 75 ml of phosphate buffer solution, agitation for 1 min, phase separation, and withdrawal of the aqueous phase.

A water soluble surfactant was used to eject the artificial red cells from the oil phase. Five grams of Renex 30 (polyoxyethylene (12) tridecyl ether supplied by ICI Americas Inc.) were dissolved in 75 ml of saline solution and added through the dip tube. The mixture was stirred for 3 min and allowed to stand. Within 5 min most of the oil had risen to the top of the jar and a dark band containing the artificial red cells appeared at the bottom of the aqueous phase. The artifical red cells were withdrawn through the dip tube, washed 3 times in saline to remove the surfactant, centrifuged and decanted. No free hemoglobin was observed in the supernatant.

To demonstrate the mechanical strength of the artifical red-cell membrane, a portion of the artificial red cells was suspended in saline solution, and the suspension was drawn into a 10 cc syringe. A 22 ga needle was placed on the syringe and the contents were forced out over a period of 30 sec to produce a shear rate of $3.63 \times 10^4$ sec. The ejected suspension was centrifuged and examined for the presence of free hemoglobin. There was no evidence of hemolysis. The artificial red cells were resuspended and forced through the needle over a period of 6 sec to produce a shear rate of $1.84 \times 10^5$ sec. Again, there was no evidence of hemolysis.

Example 2

This example demonstrates the use of an oil soluble cross-linking agent in the preparation of artificial red cells. An aqueous hemoglobin solution was prepared by the procedure described in Example 1. The hemoglobin concentration of the solution was determined to be 18.4 g/dl by the Cyanomethemoglobin Method (Henry, Clinical Chemistry, 242–3, 1969). A 45 ml portion of this hemoglobin solution was injected into an equal volume of stirred Isopar M containing 4% of ENJ 3029 in the same stirred-jar device, and stirring was continued at 4000 rpm for 5 minutes to form an emulsion of hemoglobin solution in oil. In a second, identical stirred jar device, 0.42 ml of toluene diisocyanate (TDI) was added to 75 ml of the Isopar M containing 4% of ENJ 3029, and this mixture was stirred at 200 rpm while 20 ml of the above emulsion was injected into the oil/surfactant/TDI solution. Stirring was continued for 5 minutes to allow a membrane of cross-linked hemoglobin to form around each microdroplet of hemoglobin in the emulsion. Then 0.5 g of a second surfactant, Renex 690 having an HLB of 13.5 (polyoxyethylene alkyl aryl ether from ICI Americas Inc.), which is preferentially soluble in water, was dispersed in the emulsion to break it. Also 20 ml of a 1.6% saline solution was stirred into the breaking emulsion to provide an aqueous medium for the ejected droplets. When the mixture of phases in the broken emulsion was separated by centrifugation, the artificial red cells collected in the bottom of the tube and no dissolved hemoglobin was observed in the aqueous phase. When the artificial red cells were suspended in a 5% solution of carboxymethyl cellulose, their shape changed from spherical to elipsoidal, indicating flexibility of the membrane when water was removed osmotically.

Example 3

This example demonstrates that artificial red cells can pick up and release oxygen. A hemoglobin solution prepared by the procedure described in Example 1 was deoxygenated by bubbling a stream of nitrogen through it for one hour to form a deoxyhemoglobin solution. The remainder of the procedure for forming the artificial red cells was carried out in a nitrogen atmosphere. The deoxyhemoglobin solution (19.5 g/dl) was emulsified in an equal volume of Isopar M, containing 4% of ENJ 3029 at a stirrer speed of 4000 rpm in the stirred jar device.

An aqueous suspending phase was prepared by adding 0.4% of glutaraldehyde to a phosphate buffer solution (1% of sodium chloride and 0.7% of sodium biphosphate). A 25 ml portion of the emulsion was injected into 75 ml of the suspending phase, and the mixture was stirred for 5 min at 800 rpm. The emulsion was washed three times with the phosphate buffer solution and broken by adding 0.5 g of Renex 30 (HLB of 14.5) and 40 ml of water with manual shaking. The broken emulsion was centrifuged to recover the artificial red cells.

The artificial red cells thus formed were dispersed in phosphate buffer and equilibrated with air. A 20-microliter sample of this dispersion was injected into a Lex-$O_2$-Con-TL (Lexington Instruments) and its oxygen content was measured as 4.2 volume percent. The hemoglobin content of the sample was gravimetrically determined to be 6.25%. After correcting for $O_2$ dissolved in water, the $O_2$ content was calculated to be 0.6 ml/g of hemoglobin.

Example 4

To demonstrate the use of another oil soluble solution in the preparation of artificial red cells, the procedure in Example 1 was repeated with 1% of Santone 10-10-0 (decaglycerol decaoleate from SCM Durkee Industrial Foods Group) instead of 4% of ENJ 3029. The Santone 10-10-0 is a preferentially oil soluble surfactant having an HLB of 2.0. The artificial red cells produced with either of these surfactants were similar in appearance.

We claim:

1. A process for making artificial red cells comprising the steps of:
   (a) emulsifying a stroma-free, aqueous hemoglobin solution in a surfactant-containing oil to form an emulsion comprising discrete microdroplets of said hemoglobin solution in a continuous phase of said oil;
   (b) forming, in an aqueous suspending phase, liquid membrane capsules comprising globules of said emulsion formed in (a), said globules comprising an aqueous interior phase of discrete microdroplets of hemoglobin solution and an exterior oil phase immiscible with both said aqueous interior phase and said suspending phase and wherein said suspending phase contains a water soluble cross-linking agent capable of polymerizing hemoglobin;
   (c) forming artificial red cells suspended in said globules of oil phase by maintaining said capsules in said aqueous suspending phase for a time sufficient for said cross-linking agent to polymerize hemoglobin at the surface of said hemoglobin solution microdroplets present in said capsules to form an artificial membrane around each of said microdroplets of hemoglobin solution;
   (d) separating the artificial red cells from the oil phase containing the artificial red cells; and
   (e) recovering the artificial red cells from the oil phase.

2. The process of claim 1 wherein said artificial red cells are separated from the oil phase by contacting said suspension of artificial red cells in said oil phase formed in step (c) with a second aqueous phase in the presence of a preferentially water-soluble surfactant having an HLB of at least 9 under conditions of agitation to form, suspend and break globules of the artificial red cell-containing oil phase in said second suspending phase, thereby freeing the artificial red cells.

3. The process of claim 1 wherein said artificial red cells are separated from the suspending oil phase by adding a preferentially water-soluble surfactant having an HLB of at least 9 to the aqueous suspending phase suspending the capsules of artificial red cell-containing oil phase formed in step (c) to break up the globules of oil phase and free the artificial red cells therefrom.

4. The process of claims 1, 2 or 3 wherein said artificial red cells have a large diameter no greater than about 8 microns and are capable of reversibly binding oxygen.

5. The process of claim 4 wherein said water soluble cross-linking agent comprises a dialdehyde.

6. The process of claim 4 wherein said artificial red cells consist essentially of an aqueous, stroma-free hemoglobin solution encapsulated in a membrane of polymerized, cross-linked hemoglobin.

7. The process of claim 6 wherein said water soluble cross-linking agent comprises a dialdehyde.

8. A process for making artificial cells comprising emulsifying an aqueous stroma-free hemoglobin solution in a continuous oil phase to form an emulsion comprising microdroplets of said hemoglobin solution dispersed in said oil phase wherein a cross-linking agent is present in said oil which intermolecularly cross-links hemoglobin at the surface of said microdroplets to form artificial red cells comprising said hemoglobin solution encapsulated in said polymerized hemoglobin and recovering said artificial red cells from the oil phase and wherein said cells are separated from said oil phase by contacting said cell-containing oil phase with an aqueous suspending phase in the presence of a preferentially water-soluble surfactant having an HLB of at least 9 under conditions of agitation to form, suspend and break globules of the artificial red cell-containing oil phase in the aqueous suspending phase which frees the artificial red cells from the oil phase.

9. The process of claim 8 wherein the artificial red cells so-produced have a large dimension no greater than about 8 microns and are capable of reversibly binding oxygen.

* * * * *